United States Patent [19]

Rosenberg et al.

[11] Patent Number: 6,132,659
[45] Date of Patent: Oct. 17, 2000

[54] PRODUCTION OF LENTICULAR TABLETS BY MELT CALENDERING

[75] Inventors: Joerg Rosenberg, Ellerstadt; Werner Maier, Schifferstadt; Jörg Breitenbach, Mannheim, all of Germany

[73] Assignee: BASF Aktiengesellschaft, Ludwigshafen, Germany

[21] Appl. No.: 08/860,019
[22] PCT Filed: Dec. 22, 1995
[86] PCT No.: PCT/EP95/05119
§ 371 Date: Jun. 20, 1997
§ 102(e) Date: Jun. 20, 1997
[87] PCT Pub. No.: WO96/19964
PCT Pub. Date: Jul. 4, 1996

[30] Foreign Application Priority Data

Dec. 23, 1994 [DE] Germany .............................. 44 46 467

[51] Int. Cl.[7] ..................................................... B29B 9/10
[52] U.S. Cl. ........................... 264/140; 264/141; 425/363
[58] Field of Search ...................... 264/141, 140; 425/363; 424/467, 464

[56] References Cited

U.S. PATENT DOCUMENTS

| 3,927,194 | 12/1975 | Geller ........................................ 424/467 |
| 4,880,585 | 11/1989 | Klimesch et al. ...................... 264/141 |
| 5,009,896 | 4/1991 | Becker ...................................... 424/467 |
| 5,073,379 | 12/1991 | Klimesch et al. ...................... 424/467 |
| 5,626,874 | 5/1997 | Conte et al. ............................. 424/467 |

FOREIGN PATENT DOCUMENTS 1766546 6/1968 Germany .

*Primary Examiner*—Mary Lynn Theisen
*Attorney, Agent, or Firm*—Keil & Weinkauf

[57] ABSTRACT

The present invention relates to a process for the production of lenticular tablets by melt calendering in which molding rolls with depressions in the shape of segments of an ellipsoid are used. The process according to the invention affords tablets which are easily deflashed and in which the tablet residue to be abraded when there is a displacement between the upper and lower half of the tablet is small.

11 Claims, 3 Drawing Sheets

PRODUCTION OF LENTICULAR TABLETS BY MELT CALENDERING

The present invention relates to a process for the production of lenticular tablets by molding a melt which contains an active ingredient in a calender with counter-rotating molding rolls which have on their surface depressions for receiving and molding the melt (melt calendering).

The production of tablets by calendering a melt containing an active ingredient is disclosed in DE-A 1 766 546 and U.S. Pat. No. 4,880,585. The basis of this process is the embedding of an active ingredient in a melt of a carrier, eg. fatty substances or water-soluble thermoplastic polymers. The melt is produced by melting the mixture of active ingredient, polymer and, where appropriate, other ancillary substances, for example in an extruder, and molding the melt in a downstream molding calender to give tablets which harden on cooling. The molding calender comprises a pair of counter-rotating molding rolls which have on their surface engravings (depressions) which correspond to the shape of one half of the required tablet. The tablet molding takes place in the region of contact of the two rolls by combination of the tablet composition in one depression on one roll with that in the opposite depression on the other roll. Both DE-A 1 766 546 and U.S. Pat. No. 4,880,585 describe the production of rod-shaped tablets (oblong tablets).

The production of tablets by the melt calendering process usually results, as a consequence of the compression process, in an encircling burr consisting of melt residues. This burr must be removed by deflashing techniques after the tablets have cooled. In the case of hard, brittle tablet formulations and thin burrs, this can take place in a simple manner, for example, by placing the tablets in rotating vessels in which deflashing takes place due to mutual abrasion of the tablets against one another. In the case of thick burrs or formulations capable of plastic deformation, simple deflashing is impossible. For example, deflashing of the oblong tablets described in U.S. Pat. No. 4,880,585 is not satisfactorily possible by the mentioned simple process in rotating vessels. In order to ensure adequate deflashing in such cases it is necessary to have recourse to other deflashing techniques which increase the production costs.

Because of inaccuracies in the production of the molding rolls or non-uniform rotation of the molding rolls, the depressions necessary to mold a tablet are frequently not exactly opposite to one another. The consequence of this is that the two halves of the tablet are displaced with respect to one another.

Such a displacement between the upper half and lower half of the tablet in the case of oblong tablets disclosed in U.S. Pat. No. 4,880,585 is shown in FIG. 2. In order to obtain usable tablets it is necessary to abrade the protruding tablet residues. It is evident from FIG. 2 that large amounts of tablet material must be abraded in the case of prior art oblong tablets, which is extremely time-consuming and, as a rule, associated with loss of material. DE-A 38 30 355 proposes a way of avoiding the abovementioned difficulties by molding the tablets not by calendering but after the extrusion in a conventional tableting machine at 25° C.

It is an object of the present invention to provide a process for the production of tablets in which the deflashing of the tablets and the removal of the protruding parts owing to a displacement between the tablet halves is possible in a simple way.

We have found that this object is achieved by producing tablets by melt calendering in a mold in which the angle between the plane of the burr and the tablet body is greater than 90°. Tablets of this type are lenticular in shape.

The present invention therefore relates to a process for the production of lenticular tablets by molding a melt which contains an active ingredient in a calender with two counter-rotating molding rolls which have on their surface depressions for receiving and molding the melt, wherein at least one molding roll which has depressions in the shape of segments of an ellipsoid is used.

The molding rolls of the calender which are in contact along a surface line contain, as mentioned, depressions in the shape of a segment of an ellipsoid, in each case corresponding to one half of the tablet.

The process according to the invention results, because of the depressions in the shape of segments of an ellipsoid in the molding rolls, in flat lenticular tablets. These depressions are preferably in the shape of a segment of a sphere so that the resulting tablets are round.

In the case of the tablets obtained according to the invention, the burr is in the form of a flange-like rim extending in the central plane of the tablets. The angle α between the plane of the burr and the tablet body (tangential surface at the burr) is greater than 90°, preferably greater than 135°. In a corresponding manner, the angle 2α between the upper and lower tangential surface at the burr is greater than 180°, preferably greater than 270°, see FIG. 3. Correspondingly, in the case of the depressions the angle between the tangential surface of the depression and the tangential surface of the roll at the point of intersection of the depression with the surface of the roll is less than 90°, preferably less than 45°.

Figure 1:
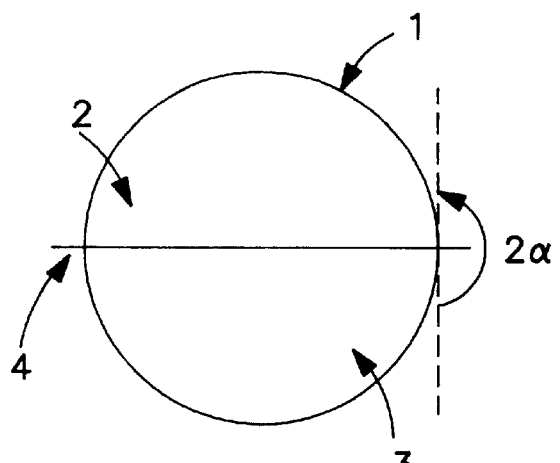
FIG. 1 is a view of an oblong tablet disclosed in U.S. Pat. No. 4,880,585 with a burr projecting at the sides.

In contrast thereto, in the prior art oblong tablet, the angle α between the plane of the burr and the tablet body is about 90° and the angle between the upper and lower tangential surface at the burr is about 180°, see FIG. 1.

This has considerable consequences for the subsequent deflashing steps. Whereas long deflashing times are required in the case of the oblong tablets, this effort is considerably reduced in the case of the tablets obtainable according to the invention since, because of the larger angle, both the frequency (better accessibility) and the intensity of the mutual contact between the tablets on deflashing increase considerably. The relatively pointed, sharp outer edges of the tablets which can be obtained according to the invention and have not yet been deflashed are additionally rounded during the deflashing so that it is finally possible to produce tablets which are identical in shape and appearance to the tablets produced conventionally, ie. by compressing granules.

Figure 4:
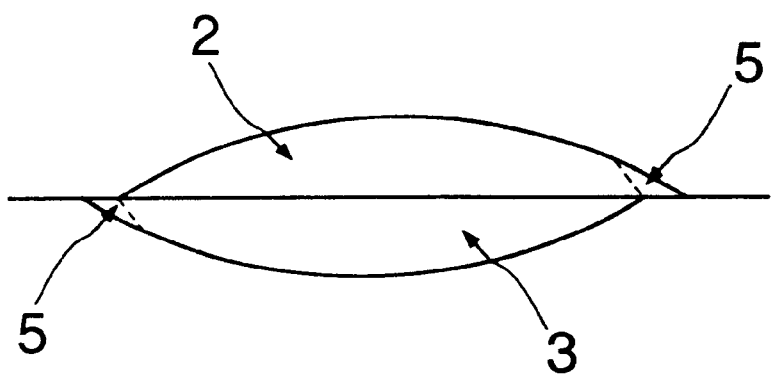
FIG. 4 is likewise a side view through a tablet obtainable according to the invention, where the upper half and lower half of the tablet are arranged with a mutual displacement.
Figure 5:
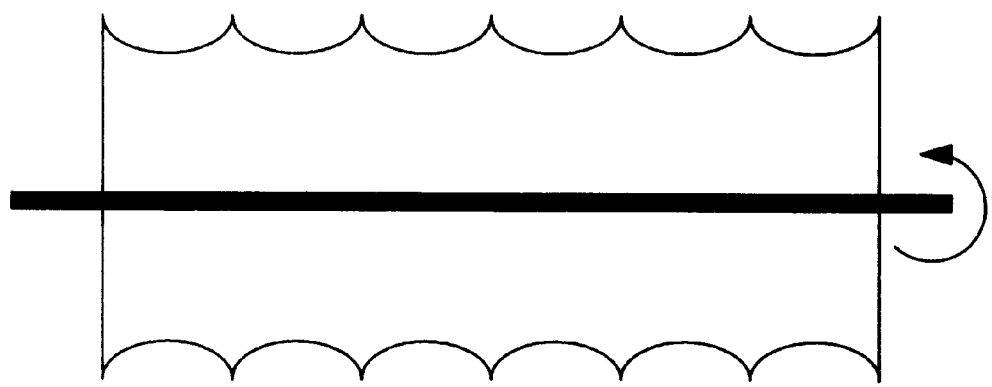
FIG. 5 is a cross-sectional view of the calender molding roll having on its surface a plurality of depressions in the shape of segments of an ellipsoid, wherein the depressions having an upper edge, and wherein the angle between the tangential surface of each depression at the upper edge and the surface of the molding roll is <90°.
Figure 6:
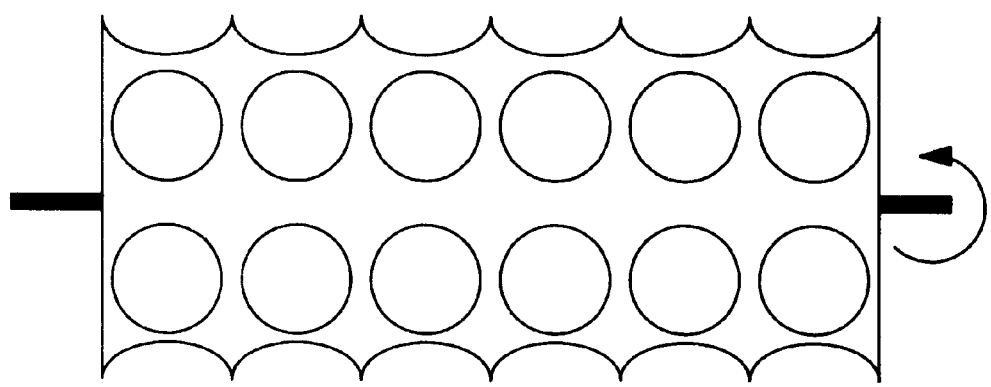
FIG. 6 is a top view of the calender molding roll having on its surface a plurality of depressions in the shape of segments of an ellipsoid, wherein the depressions having an upper edge, and wherein the angle between the tangential surface of each depression at the upper edge and the surface of the molding roll is <90°.

Another advantage of the tablets obtainable according to the invention is that the tablet material to be abraded when there is a displacement between the upper and lower half of the tablet is very small, as is evident from FIG. 4. The consequence of this is that, on the one hand, the time taken to abrade the tablet material is considerably less and, on the other hand, the specifications for the precision and rotation of the molding calender rolls employed can be reduced, which lowers the machine costs.

Figure 3:
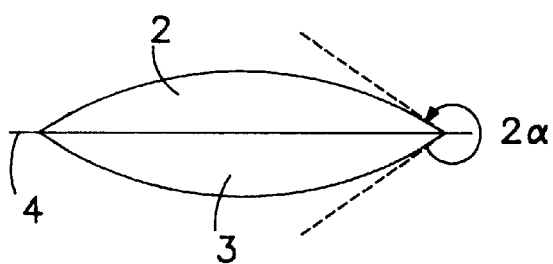
FIG. 3 is the side view of a tablet obtainable according to the invention with burr.

The problem of displacement is completely avoided if a molding roll with ellipsoidal depressions is combined with a smooth roll. This results in tablets with the shape of a segment of an ellipsoid or segment of a sphere corresponding to a half of a tablet as shown in FIG. 3 for example. This tablet can be deflashed just as easily as, for example, the tablet shown in FIG. 3.

It is also possible, if required, to produce divisible tablets. For this purpose it is possible to provide a small rib, which is often in the micrometer range, on the bottom of the depressions, which leads to the formation of the score in the finished tablets. However, it is preferable to use at least one molding roll in which the depressions are divided by at least one bar which extends essentially up to the surface of the molding roll and forms the score.

The tablets are produced starting from a mixture which contains one or more pharmaceutical active ingredients and one or more conventional ancillary substances and which becomes a paste or viscous liquid, and can therefore be extruded, by melting or softening of at least one component.

These are, in particular, mixtures containing pharmacologically acceptable polymers (with the glass transition temperature of the mixture being below the decomposition temperature of all the components of the mixture), for example polyvinylpyrrolidone (PVP), copolymers of N-vinylpyrrolidone (NVP) and vinyl acetate, copolymers of vinyl acetate and crotonic acid, partially hydrolyzed polyvinyl acetate, polyvinyl alcohol, ethylene/vinyl acetate copolymers, poly(hydroxyethyl methacrylate), copolymers of methyl methacrylate and acrylic acid, cellulose esters, cellulose ethers, polyethylene glycol or polyethylene, preferably NVP copolymers with vinyl acetate, hydroxypropylcellulose and polyethylene glycols/polyethylene oxides. The K values (according to H. Fikentscher, Cellulose-Chemie 13 (1932) 58–64 and 71–74) of the polymers are in the range from 10 to 100, preferably 12 to 70, in particular 12 to 35, for PVP preferably 12–35, in particular 12–17.

The polymeric binder must soften or melt in the complete mixture of all the components in the range from 50 to 180, preferably 60 to 130° C., so that the composition can be extruded. The glass transition temperature of the mixture must therefore always be below 180, preferably below 130° C. It is, if necessary, reduced by conventional pharmacologically acceptable plasticizing ancillary substances such as long-chain alcohols, ethylene glycol, propylene glycol, trimethylolpropane, triethylene glycol, butanediols, pentanols, hexanols, polyethylene glycols, silicones, aromatic carboxylic esters (eg. dialkyl phthalates, trimellitic esters, benzoic esters, terephthalic esters) or aliphatic dicarboxylic esters (eg. dialkyl adipates, sebacic esters, azelaic esters, citric and tartaric esters) or fatty acid esters.

Examples of conventional pharmaceutical ancillary substances, whose total amount can be up to 100% by weight based on the polymer, are extenders such as silicates or diatomaceous earth, stearic acid or salts thereof, eg. the magnesium or calcium salt, methylcellulose, lose, sodium carboxymethylcellulose, talc, sucrose, lactose, cereal or corn starch, potato flour, polyvinyl alcohol, also wetting agents, preservatives, disintegrants, absorbents, colorants, flavorings (cf., for example, H. Sucker et al. Pharmazeutische Technologie, Thieme-Verlag, Stuttgart 1978). They must be thermally stable at the temperatures used here.

Pharmaceutical active ingredients mean for the purpose of the invention all substances with a pharmaceutical effect and minimal side effects as long as they do not decompose under the processing conditions. The amount of active ingredient per dose unit and the concentration may vary within wide limits depending on the activity and rate of release. The only condition is that they suffice to achieve the desired effect. Thus, the concentration of active ingredient can be in the range from 0.1 to 95, preferably from 20 to 80, in particular 30 to 70, % by weight. It is also possible to use combinations of active ingredients. Active ingredients for the purpose of the invention are also vitamins as well as crop treatment agents and insecticides.

The process according to the invention is suitable, for example, for processing the following active ingredients:

acebutolol, acetylcysteine, acetylsalicylic acid, acyclovir, alprazolam, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkonium hydroxide, benzocaine, benzoic acid, betamethasone, bezafibrate, biotin, biperiden, bisoprolol, prazosin, bromazepam, bromhexine, bromocriptine, budesonide, bufexamac, buflomedil, buspirone, caffeine, camphor, captopril, carbamazepine, carbidopa, carboplatin, carotenoids such as β-carotene or canthaxanthin, cefachlor, cefalexin, cefatroxil, cefazolin, cefixime, cefotaxime, ceftazidime, ceftriaxone, cefuroxime, celedilin, chloramphenicol, chlorhexidine, chlorpheniramine, chlortalidone, choline, cyclosporin, cilastatin, cimetidine, ciprofloxacin, cisapride, cisplatin, clarithromycin, clavulanic acid, clomipramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphen, diazepam, diclofenac, digoxin, dihydrocodeine, dihydroergotamine, diltiazem, diphenhydramine, dipyridamole, dipyrone, disopyramide, domperidone, dopamine, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavin mononucleotide, fluconazole, flunarizine, fluorouracil, fluoxetine, flurbiprofen, furosemide, gemfibrozil, gentamicin, Ginkgo biloba, glibenclamide, glipizide, clozapine, Glycyrrhiza glabra, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, ketotifen, ketoconazole, ketoprofen, ketorolac, labetalol, lactulose, lecithin, levocarnitine, levodopa, levoglutamide, levonorgestrel, levothyroxine, lidocaine, lipase, lipoic acid, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamin mixtures or combinations and mineral salts, N-methylephedrine, naftidrofuryl, naproxen, neomycin, nicardipine, nicergoline, nicotinamide, nicotine, nicotinic acid, nifedipine, nimodipine, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, phenobarbital, pentoxifylline, phenylephrine, phenylpropanolamine, phenytoin, piroxicam, polymyxin B, povidone-iodine, pravastatin, prednisolone, bromocriptine, propafenone, propranolol, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatropin, sotalol, spironolactone, sucralfate, sulbactam, sulfamethoxazole, sulpiride, tamoxifen, tegafur, teprenon, terazosin, terbutaline, terfenadine, theophylline, thiamine, ticlopidine, timolol, tranexamic acid, tretinoin, triamcinolone acetonide, triamteren, trimethoprim, troxerutin, uracil, valproic acid, vancomycin, verapamil, vitamins $B_1$, $B_2$, $B_4$, $B_6$, $B_{12}$, $D_3$, E, K, folinic acid, zidovudine.

In a few cases, solid solutions may form. The term "solid solutions" is familiar to the skilled person, for example from the literature cited at the outset. In solid solutions of pharmaceutical active ingredients in polymers, the active ingredient is present in a molecular dispersion in the polymer.

The pharmaceutical mixture is then melted in a conventional way, preferably in an extruder, and fed to the molding calender as described, for example, in U.S. Pat. No. 4,880, 585. If necessary, the tablets are cooled after the calendering, eg. in an air or cooling bath.

In the case of sticky or highly viscous materials which are detached from the mold only with difficulty or not at all, it is expedient to use a mold release agent, for example a silicone oil or a silicone paint, or else mono-, di- and triglycerides and lecithins.

The invention is explained hereinafter by means of the figure and the examples, without limiting it.

FIG. 1 shows an oblong tablet 1 which has been obtained by the process described in U.S. Pat. No. 4,880,585. It has an encircling burr 4 which divides the tablet into an upper half 2 of the tablet and a lower half 3 of the tablet. The angle α between the plane of the burr and the tablet body (tangential area at the burr) is about 180°.

Figure 2:
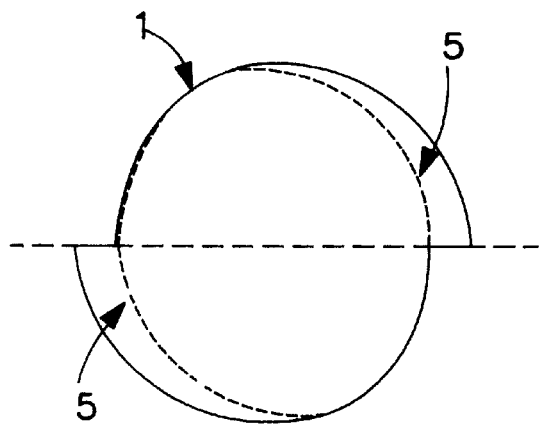
FIG. 2 is a cross-section through a corresponding oblong tablet where the upper half and lower half of the tablet are displaced with respect to one another.

FIG. 2 shows a cross-section through a corresponding oblong tablet 1 in which the upper half of the tablet is displaced with respect to the lower half of the tablet. It is evident that the tablet residue 5 to be abraded to obtain a tablet with uniform surface is considerable.

FIG. 3 is a side view of a tablet which has been obtained by the process according to the invention using two molding rolls with depressions in the shape of segments of a sphere. The burr 4 divides the tablet into an upper half 2 of the tablet and a lower half 3 of the tablet. The angle 2α between the upper and lower tangential surface at the burr is about 290°.

FIG. 4 is a side view of a tablet which essentially corresponds to that in FIG. 3 but in which the upper half 2 of the tablet is displaced with respect to the lower half 3 of the tablet. The tablet residue to be abraded is relatively small in this case.

EXAMPLE 1

Tablets of this type were produced starting from a mixture comprising 60.0% by weight of Kollidon VA-64 (BASF) (polyvinylpyrrolidone copolymer with vinyl acetate (60:40)). The mixture was extruded in a twin screw extruder (ZSK-40, Werner+Pfleiderer) under the following conditions:

Temperatures:
  Shot 1: 80° C.
  Shot 2: 100° C.
  Shot 3: 130° C.
  Shot 4: 130° C.
  Dies: 135° C.
Material throughput: 25 kg/h
Screw speed: 160 rpm The melt was fed into a molding calender with two counter-rotating molding rolls (molding roll effective width about 14 cm). The depressions in the molding rolls were such that lenticular tablets as shown in FIG. 3 were molded from the melt.

The calender and molding rolls useful for the present invention can be cooled or heated in a manner known per se and the optimum surface temperature of the rolls for the relevant processing step can be adjusted in this way.

We claim:

1. A process for the production of lenticular tablets, which process comprises: molding a melt in a calender until tablets are formed; said melt comprising an active ingredient; said calender comprising counter-rotating molding rolls which have on their surface a plurality of mutually opposite depressions in the shape of segments of an ellipsoid for receiving and molding the melt; and wherein the angle between the tangential surface of each depression at the upper edge and the surface of the molding roll is <90°; and then deflashing the tablets.

2. A process as claimed in claim 1, wherein at least one molding roll which has depressions in the shape of segments of a sphere is used.

3. A process as claimed in claim 1, wherein molding rolls provided with a release agent are used.

4. A process as claimed in claim 1, wherein a melt which contains an active ingredient and which comprises at least one pharmaceutically acceptable, water-soluble polymer is used.

5. A process as claimed in claim 1, wherein polyvinylpyrrolidone, a copolymer of N-vinylpyrrolidone and a vinyl ester, copolymers of vinyl acetate and crotonic acid, partially hydrolyzed polyvinyl acetate, polyvinyl alcohol, an ethylene/vinyl acetate copolymer, poly (hydroxyethyl methacrylate), copolymers of methyl methacrylate and acrylic acid, cellulose eaters, cellulose ethers or polyethylene glycol is used as polymer.

6. A process as claimed in claim 1, wherein at least one molding roll in which the depressions are divided by at least one bar which extends essentially up to the surface of the molding roll and forms a score is used.

7. The process of claim 1, wherein the angle between the tangential surface of the depression at the upper edge and the surface of the molding rolls is <45°.

8. A calender molding roll having on its surface a plurality of depressions in the shape of segments of an ellipsoid; said depressions having an upper edge; wherein the angle between the tangential surface of each depression at the upper edge and the surface of the molding roll is <90°.

9. The calender molding roll defined in claim 8, wherein the angle between the tangential surface of the depression at the upper edge and the surface of the molding roll is <45°.

10. The calender molding roll defined in claim 8, wherein said depressions are in the shape of a sphere.

11. A calender molding roll as claimed in claim 8, wherein the depressions are divided by at least one bar which extends up to the surface of the molding roll.

* * * * *

UNITED STATES PATENT AND TRADEMARK OFFICE
CERTIFICATE OF CORRECTION

PATENT NO.: 6,132,659

DATED: October 17, 2000

INVENTOR(S): ROSENBERG et al.

It is certified that error appears in the above-identified patent and that said Letters Patent is hereby corrected as shown below:

Col. 6, claim 5, line 45, "cellulose eaters" should be --cellulose esters--.

Signed and Sealed this

Eighth Day of May, 2001

Attest:

NICHOLAS P. GODICI

Attesting Officer     Acting Director of the United States Patent and Trademark Office